ical Industries
United States Patent [19]

Thompson et al.

[11] 3,952,034
[45] Apr. 20, 1976

[54] CARBONYLATION OF OLEFINS AND ACETYLENES

[75] Inventors: David Thomas Thompson, Frodsham; Reginald Jackson, Middlewich, both of England

[73] Assignee: Imperial Chemical Industries Limited, London, England

[22] Filed: Dec. 3, 1973

[21] Appl. No.: 421,348

Related U.S. Application Data

[63] Continuation of Ser. No. 126,319, March 19, 1971, abandoned.

[30] Foreign Application Priority Data

Mar. 25, 1970 United Kingdom............. 14415/70
Sept. 4, 1970 United Kingdom............. 42532/70

[52] U.S. Cl................ 260/410.5; 260/468 M; 260/476 R; 260/479 R; 260/485 R; 260/486 AC; 260/497 A; 260/498; 260/514 M; 260/515 R; 260/533 A; 260/537 R; 260/410.9 R

[51] Int. Cl.² .................................... C07C 55/18
[58] Field of Search ..... 260/537 R, 533 AN, 497 B, 260/410.9, 410.5

[56] References Cited
UNITED STATES PATENTS

| | | | |
|---|---|---|---|
| 3,043,872 | 7/1962 | Roberts et al.................. | 260/537 R |
| 3,453,299 | 7/1969 | Claridge............................ | 260/429 |
| 3,468,927 | 9/1969 | Duke et al. ........................ | 260/537 |
| 3,579,552 | 5/1971 | Craddock et al. ........... | 260/533 AN |
| 3,597,460 | 8/1971 | Thompson ...................... | 260/438.5 |
| 3,622,607 | 11/1971 | Fenton............................. | 260/429 J |
| 3,661,949 | 5/1972 | Fenton......................... | 260/533 AN |
| 3,717,670 | 2/1973 | Schultz ............................. | 260/532 |

OTHER PUBLICATIONS

Bittler et al. Angev. Chem. Inter. Edit./Vol. 7 (1968) No. 5, pp. 329–335.

*Primary Examiner*—Lorraine A. Weinberger
*Assistant Examiner*—P. J. Killos
*Attorney, Agent, or Firm*—Cushman, Darby & Cushman

[57] ABSTRACT

Olefins and acetylenes are carbonylated to a carboxylic acid or ester using a homogenous catalyst system comprising palladium together with iron or a metal of Groups IVA, VA or IIIB, the catalyst being either a polynuclear complex incorporating both metals, or a mixture of a soluble palladium salt and metal halide. Starting with cyclic di-olefins, such as cyclo-octadiene, the product cycloalkenyl carboxylic acid or ester may be cleaved to give acyclic dicarboxylic acids, such as azelaic acid.

13 Claims, No Drawings

CARBONYLATION OF OLEFINS AND ACETYLENES

This is a continuation of application Ser. No. 126,319 filed Mar. 19, 1971, now abandoned.

This case relates to carbonylation reactions, and in particular to the carbonylation of olefinically and acetylenically unsaturated compounds to carboxylic acids or esters.

It has been proposed to use complexes of Pd(II) as homogenous catalysts for the carbonylation of olefins; but, in general, the previous processes tend to require comparatively high pressures of carbon monoxide, with a consequent need for expensive equipment.

A general review of the carbonylation of olefins using palladium complexes as catalysts appears in Angew. Chem. 80, 352, (1968) (International Edition, Vol. 7 (1968), p. 329) and references therein.

We have now discovered that catalyst systems useful for carbonylation may be obtained by employing palladium in conjunction with certain other metals as co-catalysts.

According to the present invention, we provide a process for the conversion of olefinically or acetylenically unsaturated compounds to carboxylic acids or esters which comprises reacting the unsaturated compound with carbon monoxide and either water or an alcohol or a phenol in the presence of a homogeneous catalyst system containing either a polynuclear complex incorporating palladium in combination with at least one further metal selected from the group consisting of iron and the metals of Groups IVB, VB and IIIA of the Periodic Table, or a palladium compound in admixture with a halide of at least one of the above further metals.

All references to the Periodic Table are to the edition of the Periodic Table of the Elements printed inside the back cover of the Handbook of Chemistry and Physics, 46th Edition (1965) The Chemical Rubber Company.

By homogeneous catalyst system we mean a compound or mixture of compounds which is soluble in the liquid phase of the reaction mixture under the reaction conditions employed.

Suitable unsaturated starting materials include aliphatic compounds, for example butenes, butadiene, pentadienes, or octenes, and cycloaliphatic compounds, for example cyclohexene, cyclo-octene, cyclo-octadienes, cyclododecene, cyclododecadienes, or cyclododecatrienes. Aralkenes, for example styrene, may also be employed.

The starting material may be a simple hydrocarbon or may bear incidental, inert substituents on the carbon skeleton, provided that these do not interfere with carbonylation at the site of unsaturation.

The water, alcohol, or phenol act as a hydrogen source, and also determine the structure of the product. Thus, the products will be free acids if water is employed, while the presence of an alcohol or phenol will result in the production of an ester.

The alcohol or phenol employed will depend on the desired ester. Alcohols may be primary, secondary or tertiary, aliphatic or aromatic as desired. Thus, for example, methanol, ethanol butanol, iso-butanol, cyclohexanol, and benzyl alcohol may all be employed, depending on the structure of the desired ester.

Polyhydric alcohols or polybasic phenols may be used to produce hydroxy esters or derivatives thereof, with suitable choice of reaction conditions.

For monohydric alcohols or monobasic phenols, the reaction scheme may thus be represented as

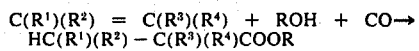

where $R^1$, $R^2$, $R^3$ and $R^4$, which may be the same or different, represent hydrogen or an organic group, and where R is an organic group. The double bond may be part of an alicyclic ring system.

A similar reaction scheme is applicable to alkynes.

Polyenes tend to undergo carbonylation at only one site of unsaturation, but several sites may be carbonylated by suitable choice of reaction conditions. Alkynes may be made to produce $\alpha,\beta$-unsaturated carboxylic acids or esters, or carbonylation can be continued to give the diacid or ester.

For reasons of simplicity, the following discussion will be confined to the case where the catalyst system contains two metals only, but it is to be understood that further metals may also be present as required.

The homogeneous catalyst composition may be a mixture of a soluble palladium compound with a halide of a further metal listed above, or may be a polynuclear complex incorporating both metals. U.S. Pat. Nos. 3,519,663 and 3,453,299 describe and claim dinuclear bridged transition metal organic complexes in which the transition metals are different, in which the bridging ligands are univalent with respect to one of the metal atoms and do not incorporate chelating ligands, and in which other ligands are present as required to satisfy the co-ordination numbers and valencies of the transition metal atoms. Iron/palladium complexes within the scope of that patent are useful in the process of our invention.

A suitable complex is a trans-bis(diarylphosphidoirontetracarbonyl)-$\mu,\mu$-dihalodipalladium

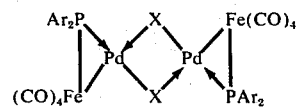

where Ar is an aryl group and X is halogen. These complexes may be prepared by condensing together $\pi$-allylpalladium halide dimer and diarylphosphine-iron tetracarbonyl in solution in an inert solvent, as claimed in U.S. Pat. No. 3,597,460.

The relative proportions of the two metals in the catalyst composition are not critical, but generally, an atomic ratio of about 1:1 is convenient. When using a mixture of a palladium compound and a metal halide, it is preferred to employ an atomic ratio of further metal to palladium of from about 1:1 to about 30:1, preferably from about 1:1 to about 20:1.

As mentioned above, the two metals may be present as a preformed complex, or as a mixture of a palladium compound with a metal halide. Preferred halides are the chlorides, bromides and iodides, particularly the chlorides. Preferably, the metal is in a high oxidation state, as in titanium or zirconium tetrachloride or ferric chloride. Aluminium and ferric chlorides are particularly advantageous, and are therefore preferred.

Preferably the palladium compound is an organic complex, such as phosphine, and it is desirable that it shares a common anion with the metal halide. Thus, for example, palladium may be present as a bis(tri-aryl-phosphine)palladium dihalide or as a dinuclear complex such as π-allyl palladium halide dimer or tri-aryl phosphine palladium dihalide dimer.

Alternatively, both the palladium and the further metal may be present as simple salts, though it may be necessary for a ligand-forming reagent, for example a phosphine, to be present in addition to the salts, in order to aid solution of the catalyst components in the reaction medium, or to improve catalyst stability. Aryl phosphines are advantageous as ligand-forming reagents.

The catalyst composition may be stabilised by inclusion of excess of the appropriate ligand-forming reagent.

Reaction conditions are not critical, though the temperature stability of the catalyst in the reaction medium may become a limiting factor as the temperature is raised. The dependence of catalyst utilisation on the temperature and pressure employed may vary with particular catalyst combinations, but a suitable balance of temperature and pressure for any catalyst composition can be readily established by routine experimentation.

The rate of reaction slows down at low temperatures. For mixtures of a palladium complex with a metal halide, a convenient lower temperature limit for economic rates of reaction is about 45° to 50°C, but lower temperatures may be employed if desired, particularly in conjunction with high pressures.

As stated above, the upper temperature limit is mainly dictated by the temperature stability of the catalyst in the reaction medium. Catalyst utilisation falls off as the temperature increases beyond an optimum value, the upper limit for economic operation being about 150°C, but the exact limit will depend on the catalyst utilisation required, and on the pressure employed.

Partial pressure of carbon monoxide affects catalyst utilisation, as well as reaction rate. It is possible to work at ambient pressure, but, in general, it is preferred to use a carbon monoxide pressure of at least 25 atmospheres. The upper pressure limit is mainly dictated by economic considerations, high pressure equipment being expensive. It is found, however, that, with some catalysts, at high pressures catalyst utilisation tends to fall somewhat, depending on the temperature. For catalysts operated at about 100°C, a convenient upper pressure limit is about 300 atmospheres, but higher pressures may be used as required.

A convenient balance of reaction rates and catalyst utilisation may be achieved at temperatures around 100° to 110°C, in combination with carbon monoxide partial pressures of about 100–150 atmospheres.

The carbon monoxide may be diluted with an inert gas, such as nitrogen, if required, but it is preferred to employ an atmosphere of pure carbon monoxide.

Yields of product may be increased by working under oxygen-free conditions, and it is therefore advantageous to deoxygenate the reagents before commencement of reaction.

For mono-olefins, the proportions of olefin and water, alcohol, or phenol may be varied as desired, and any reagent in excess may be recycled for use in a repetition of the carbonylation reaction.

It is a feature of our invention that, using catalysts as described, the degree of carbonylation of polyenes and acetylenes may be closely controlled by varying the stoichiometry of the reaction, together with reaction conditions. Thus, butadiene, cyclo-octadiene, or cyclododecatriene, in admixture with water or an alcohol or phenol in a molar ratio of 1:1 will give the corresponding mono-carboxylic acid or ester, with essentially no di- or tri-carbonylated products. Similarly, a mixture of an alkyne and water or an alcohol or phenol in a molar ratio of 1:1 will be carbonylated essentially to an $\alpha,\beta$-unsaturated carboxylic acid or ester.

Polycarboxylic acids or esters can be produced by increasing the amount of water, or alcohol or phenol, as determined by the stoichiometry of the reaction, in combination with the use of suitable reaction conditions, higher temperatures and pressures favouring the production of polycarboxylic acids and esters. Reaction conditions may readily be determined by routine experimentation.

The amount of catalyst employed will depend on reaction conditions, particularly as these affect catalyst utilisation. Routine experimentation will readily show, for any chosen reaction conditions, the expected yield of product for unit quantity of catalyst, and the amount of catalyst required for a given reaction may thus be determined.

A convenient lower limit for palladium concentration in the liquid phase of the reaction mixture is about $0.2 \times 10^{-3}$M. The upper limit is dictated by solubility considerations, and may conveniently be about $3 \times 10^{-3}$M but higher concentrations of palladium may be employed, provided that the catalyst composition remains soluble in the liquid phase of the reaction mixture under the prevailing conditions of temperature and pressure.

When the catalyst metals are present in a preformed complex, the catalyst stability is greater in acid conditions, and it is therefore preferable for the reaction medium to be rendered acid. Added acids may be mineral acids, for example, hydrochloric, sulphuric, or phosphoric acids, or organic acids, for example acetic acid, benzoic acid, or $p$-toluene sulphonic acid. When mixtures of metal compounds are employed, as opposed to a preformed complex containing both metals, it is preferable to operate without addition of acid to the reaction mixture.

Amounts of added acid are not critical, but corrosion of the reaction vessel may become a problem with strongly acid reaction media. A convenient amount of mineral acid is upto 5% by volume.

It is preferred that the reaction mixture comprises only the reacting materials and the catalyst composition, together with added acid, as appropriate. However, in order to increase solubility of the components, it may be desirable to incorporate a liquid solvent or diluent which is inert under the reaction conditions. Suitable solvents include saturated or aromatic hydrocarbons, for example, pentane, cyclohexane, gasoline hydrocarbons, benzene and toluene. Alternatively, ketones or ethers may be employed.

The product acids or esters may be separated from unreacted starting material by conventional means, for example, distillation or solvent extraction.

Convenient starting materials are cyclic olefins including two double bonds. Both double bonds may be within the ring, as in cyclo-octadiene or cyclododecadiene, or one double bond may be in a substituent group of the ring, as in vinylcyclohexene. These starting materials may be carbonylated to a cycloalkenyl carboxylic acid or ester, and the product acids or esters may themselves be converted by alkaline cleavage at elevated temperature to an acyclic dicarboxylic acid. Preferably, the product resulting from the carbonylation step is hydrolysed and the reaction mixture is freed of alcohol prior to the cleavage of the cycloalkenyl ring.

It is to be noted that, in this reaction scheme, it is not necessary to purify the product cycloalkenyl ester, since the crude reaction mixture from the carbonylation process may be used as such as a feedstock for acyclic dicarboxylic acid production. The catalyst metals may be recovered during the conversion to diacid.

A particularly advantageous starting material is cyclo-octa-1,5-diene, since this is readily carbonylated to a cyclo-oct-4-ene-1-carboxylate, which may itself be converted by alkaline cleavage at elevated temperature to azelaic acid (heptane-1,7-dicarboxylic acid), a useful intermediate in the production of polyamides. This reaction may be shown schematically as

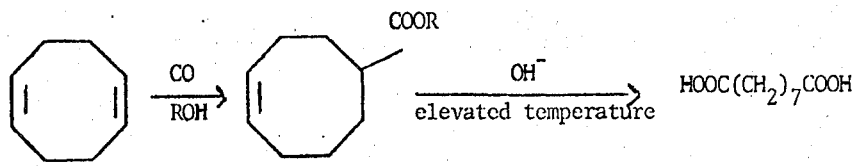

where R is an organic group or hydrogen. Preferably, when R is an organic group the product cyclo-oct-4-ene-1-carboxylate is hydrolysed and the resultant alcohol removed before commencement of the conversion to azelaic acid.

It has been found that essentially no isomerisation to cyclo-octa-1,3-diene need occur during the carbonylation reaction, so that unreacted cyclo-octadiene may be recycled as such for use in a repetition of the reaction, as required.

The carbonylation may be performed batchwise or continuously, as required.

The invention is illustrated by the following Examples, in which parts by weight and parts by volume bear the same relation as do kilograms and liters. Catalyst utilisation, where applicable, is expressed as moles of product per mole of palladium compound. Yields of products are expressed as mole % calculated on the basis of initial olefin or acetylene. In all cases where yields are less than theoretical, the balance was essentially pure unreacted starting material.

EXAMPLE 1

Redistilled oct-1-ene (40 parts by volume), redistilled absolute ethanol (40 parts by volume) and a palladium-iron complex of formula:

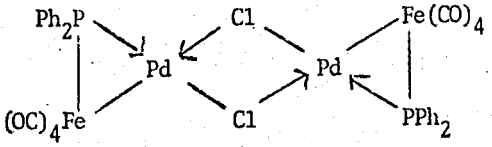

where Ph is phenyl, (0.2 parts by weight) were charged to an autoclave having a capacity of 300 parts by volume. The autoclave was flushed with carbon monoxide and anhydrous hydrogen chloride was added (about 4% by volume of the ethanol).

The autoclave was pressurized with sufficient carbon monoxide to give a pressure of 100 atmospheres when the autoclave was at working temperature. The autoclave was sealed and heated to 103° to 107°C. Reaction was continued for 3 hours, further carbon monoxide being added as required to maintain the pressure. The autoclave was then cooled and the reaction mixture was shaken thoroughly with water and extracted with diethyl ether.

Distillation of the ethereal layer gave 46 parts by volume of a mixture of ethyl octane-2-carboxylate and ethyl octane-1-carboxylate, in a molar ratio of 55:45. The yield of esters was 83%.

For comparison, a repeat of this experiment with the palladium-iron complex replaced by bis(triphenylphosphine) palladium dichloride (0.4 parts by weight) gave only 38.5 parts by volume of the two esters, in the same molar ratio. The yield of esters was 69.5%.

EXAMPLE 2

The procedure of Example 1 was repeated, but at a temperature of 75°C.

Reaction time was 6 hours, and the amount of product was 40 parts by volume, as an equimolar mixture of ethyl octane-2-carboxylate and ethyl octane-1-carboxylate. The yield of esters was 73%.

A comparative experiment using bis(triphenylphosphine) palladium dichloride (0.4 parts by weight) as catalyst gave only 13 parts by volume of products, the 2-carboxylate/1-carboxylate molar ratio being 55:45. The yield of esters was 24%.

EXAMPLE 3

The procedure of Example 1 was repeated, but at a temperature of 75°C and a carbon monoxide pressure of 50 atmospheres.

Reaction time was 6 hours, and 25 parts by volume of products were obtained, as a mixture of ethyl octane-2-carboxylate and ethyl octane-1-carboxylate in a molar ratio of 55:45. The yield of esters was 45.5%.

A comparative experiment using bis(triphenylphosphine) palladium dichloride (0.4 parts by weight) as catalyst gave only 2 parts by volume of products, in the same proportions. The yield of esters was 3.5%.

EXAMPLE 4

Cyclo-octa-1,5-diene (90 parts by volume), which had been redistilled under nitrogen, and redistilled absolute ethanol (45 parts by volume) were charged to a 300 volume autoclave, together with bis(triphenylphosphine) palladium dichloride (0.07 parts by weight) and anhydrous ferric chloride (0.2 parts by weight).

The autoclave was flushed with carbon monoxide and then pressurised with sufficient carbon monoxide to give a pressure of 100 atmospheres when the autoclave was at working temperature. The autoclave was sealed and heated to 105° to 108°C. Reaction was continued for 4 hours, the carbon monoxide being replenished as required to maintain the pressure.

The autoclave was allowed to cool and was vented. 62 parts by volume of product were obtained and this was identified by gas-liquid chromatography, using a 10% "Carbowax" column, as ethyl cyclo-oct-4-ene-1- carboxylate. (Carbowax is a Registered Trade Mark).

The yield of ester was 46.5%, and catalyst utilisation was 3,400 moles/mole.

EXAMPLE 5

The procedure of Example 4 was repeated, but with the addition of p-toluene sulphonic acid (0.2 parts by weight) to the reaction mixture, and with the amount of ferric chloride decreased to 0.025 parts by weight.

70 parts by volume of ethyl cyclo-oct-4-ene-1-carboxylate were obtained, a yield of 53.5%. Catalyst utilisation was 3,900 moles/mole.

A comparative experiment, omitting the ferric chloride, gave only 51 parts by volume of the ester, a yield of 38.2%. Catalyst utilisation was 2,800 moles/mole.

EXAMPLE 6

The procedure of Example 4 was repeated with the ferric chloride replaced by anhydrous aluminium chloride (0.2 parts by weight).

After 2 hours reaction, 122 parts by volume of ethyl cyclo-oct-4-ene-1-carboxylate were obtained. Catalyst utilisation was 6700 moles/mole.

EXAMPLE 7

The procedure of Example 4 was repeated with the ferric chloride replaced by zirconium tetrachloride (0.2 parts by weight).

After 2 hours reaction, 110 parts by volume of ethyl cyclo-oct-4-ene-1-carboxylate were obtained. Catalyst utilisation was 6000 moles/mole.

EXAMPLE 8

The procedure of Example 4 was repeated with the ferric chloride replaced by titanium tetrachloride (0.2 parts by weight).

After 2 hours reaction, 112 parts by volume of ethyl cyclo-oct-4-ene-1-carboxylate were obtained. Catalyst utilisation was 6050 moles/mole.

A number of experiments were performed on the carbonylation of cyclo-octa-1,5-diene. In all cases, the cyclo-octadiene, which had been redistilled under nitrogen, was charged to a 300 volume autoclave, together with a quantity of water, an alcohol, or a phenol (the hydroxyl compound) which was free of molecular oxygen. Also charged to the autoclave were appropriate amounts of bis(triphenylphosphine)palladium dichloride and a metal halide. The autoclave was flushed with carbon monoxide which had been deoxygenated and dried by passing it through two columns packed with freshly prepared finely divided copper, followed by a column packed with molecular sieve (type 5A). The autoclave was then pressurised with deoxygenated carbon monoxide and heated to 105°–108°C. Further carbon monoxide was added as required during reaction in order to maintain the appropriate pressure.

On completion of reaction, the autoclave was allowed to cool and was vented. Products were identified by gas-liquid chromatography.

The results are shown in Table 1.

TABLE 1

| Example No. | Amount of cyclo-octadiene Parts by volume | Amount of palladium complex Parts by weight | Metal Halide | Amount of Metal Halide Parts by weight | Hydroxyl Compound | Amount of Hydroxyl Compound Parts by volume |
|---|---|---|---|---|---|---|
| 9 | 90 | 0.1 | $FeCl_3$ | 0.2 | Ethanol | 45 |
| 9A (for comparison) | 90 | 0.1 | — | — | Ethanol | 45 |
| 10 | 90 | 0.1 | $FeCl_3$ | 0.4 | Ethanol | 45 |
| 11 | 90 | 0.1 | $FeCl_3$ | 0.2 | Methanol | 45 |
| 12 | 80 | 0.07 | $FeCl_3$ | 0.2 | n-Butanol | 55 |
| 13 | 80 | 0.07 | $FeCl_3$ | 0.2 | 2-Butanol | 55 |
| 14 | 80 | 0.07 | $FeCl_3$ | 0.2 | iso-Butanol | 55 |
| 15 | 80 | 0.07 | $FeCl_3$ | 0.2 | iso-Propanol | 45 |
| 16 | 75 | 0.2 | $AlCl_3$ | 0.6 | t-Butanol | 50 |
| 17 | 70 | 0.2 | $AlCl_3$ | 0.6 | Benzyl alcohol | 70 |
| 18 | 70 | 0.2 | $AlCl_3$ | 0.6 | Cyclohexanol | 70 |
| 19 | 65 | 0.2 | $AlCl_3$ | 0.6 | Ethylene[4] glycol | 35 |
| 20 | 25 | 0.1 | $AlCl_3$ | 0.2 | Water[5] | 4 |
| 21 | 45 | 0.1 | $AlCl_3$ | 0.4 | 2,3-Butane[4] diol | 40 |
| 22 | 50 | 0.15 | $AlCl_3$ | 0.4 | Ethanol | 70 |
| 23 | 65 | 0.2 | $AlCl_3$ | 0.8 | Phenol | 55 parts by weight |
| 24 | 90 | 0.1 | $AlBr_3$ | 0.4 | Ethanol | 45 |
| 25 | 90 | 0.035 | $AlCl_3$ | 0.2 | Ethanol | 45 |
| 26 | 90 | 0.1 | $NbCl_5$ | 0.4 | Ethanol | 45 |

| Example No. | Pressure atm. | Reaction Time hrs. | Product | Amount of product Parts by volume | Yield % |
|---|---|---|---|---|---|
| 9 | 100 | 4 | Ethyl cyclo-oct-4-ene-1-carboxylate | 117 | 87.5[1] |
| 9A (for comparison) | 100 | 4 | Ethyl cyclo-oct-4-ene-1-carboxylate | 63 | 47[2] |
| 10 | 100 | 4 | Ethyl cyclo-oct-4-ene-1-carboxylate | 129 | 97[3] |
| 11 | 102 | 2 | Methyl cyclo-oct-4-ene-1-carboxylate | 37 | 30 |
| 12 | 102 | 2 | Butyl cyclo-oct-4-ene-1-carboxylate | 69 | 56 |
| 13 | 102 | 2 | 1-Methylpropyl cyclo-oct- | 48 | 39 |

TABLE 1-continued

| Example No. | Amount of cyclo-octadiene Parts by volume | Amount of palladium complex Parts by weight | Metal Halide | Amount of Metal Halide Parts by weight | Hydroxyl Compound | Amount of Hydroxyl Compound Parts by volume |
|---|---|---|---|---|---|---|
| 14 | 102 | 2 | | 4-ene-1-carboxylate 2-Methylpropyl cyclo-oct-4-ene-1-carboxylate | 67 | 49 |
| 15 | 102 | 2 | | iso-Propyl cyclo-oct-4-ene-1-carboxylate | 65 | 51 |
| 16 | 204 | 5 | | t-Butyl cyclo-oct-4-ene-1-carboxylate | 48 | 37 |
| 17 | 204 | 5 | | Benzyl cyclo-oct-4-ene-1-carboxylate | 80 | 56 |
| 18 | 204 | 3 | | Cyclohexyl cyclo-oct-4-ene-1-carboxylate | 97 | 72 |
| 19 | 136 | 4 | | 2-Hydroxyethyl cyclo-oct-4-ene-1-carboxylate | 50 | 48 |
| 20 | 136 | 2 | | (cyclo-oct-4-ene-1-carboxylic acid | 29 | 88 |
| 21 | 136 | 4 | | 1-Methyl-2-hydroxy-propyl cyclo-oct-4-ene-1-carboxylate | 30 | 38 |
| 22 | 340 | 8 | | Diethyl cyclo-octene-dicarboxylates | 60 | 48 |
| 23 | 136 | 4 | | Phenyl cyclo-oct-14-ene-1-carboxylate | 25 | 26 |
| 24 | 102 | 3 | | Ethyl cyclo-oct-4-ene-1-carboxylate | 46 | 35 |
| 25 | 102 | 2 | | Ethyl cyclo-oct-4-ene-1-carboxylate | 41 | 30 |
| 26 | 102 | 2 | | Ethyl cyclo-oct-4-ene-1-carboxylate | 109 | 82 |

[1] Catalyst utilisation - 4500 moles/mole
[2] Catalyst utilisation - 2400 moles/mole
[3] Catalyst utilisation - 5000 moles/mole
[4] Acetone (40 parts by volume) also present as co-solvent
[5] Acetone (60 parts by volume) also present as co-solvent Gas-liquid chromatographic analysis of unreacted starting material in Examples 4 to 26 showed that there was essentially no cyclo-octa-1,3-diene present.

The general procedure of Examples 9 to 26 was repeated, using different unsaturated compounds as starting materials. The results are shown in Table 2.

TABLE 2

| Example No. | Starting Material | Amount of Starting Material Parts by volume | Amount of palladium complex Parts by weight | Metal Halide | Amount of Metal Halide Parts by weight | Hydroxyl Compound |
|---|---|---|---|---|---|---|
| 27 | Styrene | 60 | 0.1 | AlCl₃ | 0.4 | Ethanol |
| 28 | 4-Vinyl-cyclo-hex-1-ene | 90 | 0.1 | AlCl₃ | 0.2 | Ethanol |
| 29 | Oct-1-ene | 90 | 0.1 | AlCl₃ | 0.2 | Ethanol |
| 30 | Hex-1-yne | 80 | 0.1 | AlCl₃ | 0.2 | Ethanol |
| 31 | Cyclo-hexene | 80 | 0.3 | AlCl₃ | 1.0 | Ethanol |
| 32 | Cyclo-octa-1,3-diene | 90 | 0.3 | AlCl₃ | 0.6 | Ethanol |
| 33 | Cyclododeca-1,5,9-triene | 70 | 0.3 | AlCl₃ | 1.5 | Ethanol |

| Example No. | Amount of Hydroxyl Compound Parts by volume | Pressure atm. | Reaction Time hrs. | Product | Amount of Product Parts by volume | Yield % |
|---|---|---|---|---|---|---|
| 27 | 30 | 102 | 3 | Ethyl 2-phenyl propionate | 75 | 95 |
| 28 | 45 | 102 | 2 | Ethyl 2-(3-cyclo-hexenyl)propionate | 110 | 98 |
| 29 | 40 | 102 | 4 | Ethyl octane-carboxylates[1] | 56 54 | 54 |
| 30 | 40 | 102 | 5 | Ethyl heptenoate | 45 | 40 |
| 31 | 40 | 238–272 | 4 | Ethyl cyclo-hexyl-carboxylate | 25 | 23 |
| 32 | 45 | 272 | 4 | Ethyl cyclo-oct-2-ene-1-carboxylate | 42 | 31 |
| 33 | 20 | 272 | 6 | Ethyl cyclododeca-4,8-diene-1-carboxylate | 17 | 20 |

[1] Approximately equimolar proportions of 1-carboxylate and 2-carboxylate

EXAMPLE 34

The general procedure of Examples 9 to 26 was repeated, using 90 parts by volume of cyclo-octa-1,5-diene, 45 parts by volume of ethanol and a catalyst composition consisting of sodium tetrachloropalladite (0.05 parts by weight), triphenyl phosphine (0.075 parts by weight) and ferric chloride (0.2 parts by weight).

After 2 hours at 105°–108°C and 102 atmospheres, 88 parts by volume of ethyl cyclo-oct-4-ene-1-carboxylate were obtained, a yield of 67%.

EXAMPLE 35

The procedure of Example 34 was repeated with the catalyst composition replaced by a mixture of triphenylphosphinepalladium dichloride dimer (0.06 parts by weight) and aluminium chloride (0.2 parts by weight).

99 parts by volume of ethyl cyclo-oct-4-ene-1-carboxylate were obtained, a yield of 75%.

EXAMPLE 36

Cyclo-octa-1,5-diene (90 parts by volume), which had been redistilled under nitrogen, and redistilled absolute ethanol (45 parts by volume) were charged to a 300 volume glass-lined autoclave, together with bis(-triphenylphosphine) palladium dichloride (0.07 parts by weight) and anhydrous aluminium chloride (0.2 parts by weight).

The autoclave was flushed with carbon monoxide and then pressurised with sufficient carbon monoxide to give a pressure of 100 atmospheres when the autoclave was at working temperature. The autoclave was heated to 105° to 108°C and the carbon monoxide was replenished as required to maintain the pressure.

After 2 hours reaction, the autoclave was allowed to cool and was vented. A portion of the autoclave contents, containing 40 parts by weight of ethyl cyclo-oct-4-ene-1-carboxylate, was mixed with water (100 parts by volume) and sodium hydroxide (21 parts by weight). The mixture was heated under reflux for 2 hours, when metallic palladium precipitated out. This was removed by filtration, and the filtrate was poured into water (350 parts by volume) and acidified with excess concentrated hydrochloric acid to give cyclo-oct-4-ene-1-carboxylic acid as a yellow oil, which was extracted with diethyl ether (3 × 200 parts by volume). The ethereal solution was dried over sodium sulphate and the ether was evaporated off to give 32.5 parts by weight of the cyclo-octene acid. This acid was mixed with water (400 parts by volume) and sodium hydroxide (20 parts by weight) and heated in an autoclave at 320°C for 1.5 hours. The autoclave was cooled and the contents filtered, after addition of a small amount of charcoal, in order to remove inorganic materials. The filtrate was acidified with concentrated hydrochloric acid and allowed to stand overnight, to give an aqueous suspension of azelaic acid. The azelaic acid was recovered by filtration and the aqueous mother liquor was extracted with diethyl ether. The ethereal solution was dried over sodium sulphate and the ether was evaporated off. The solid residue was combined with the azelaic acid recovered by filtration, and the product was dried in a vacuum oven to give 38.6 parts by weight of crude azelaic acid.

Recrystallisation of the azelaic acid from toluene gave 31.0 parts by weight of crystals (melting point 107°–108°C), and a further 4.0 parts by weight (melting point 106°–107°C) were recovered from the toluene mother liquor.

The yield of azelaic acid was 85% calculated on the basis of the ethyl cyclo-oct-4-ene-1-carboxylate and 78% calculated on the basis of initial cyclo-octadiene.

No organic by-products were detected by gas-liquid chromatographic analysis.

What we claim is:

1. A process for the preparation of acyclic dicarboxylic acids in which
   a. a cyclic olefin selected from the group consisting of cycloalkadienes and alkenylcycloalkenes is carbonylated to a cycloalkenyl carboxylic acid or ester by reaction with carbon monoxide and a hydroxylic compound selected from the group consisting of water, alcohols, and phenols in the presence of a homogeneous catalyst composition including palladium and aluminum, the catalyst composition being a polynuclear organic complex incorporating palladium in combination with aluminum or being a mixture of a soluble palladium compound with a chloride of the further metal,
   b. the reaction mixture resulting from the above carbonylation reaction is heated to an elevated temperature under alkaline conditions to induce cleavage of the cycloalkenyl ring, and
   c. the acyclic dicarboxylic acid is isolated from the reaction mixture.

2. A process for the preparation of acyclic dicarboxylic acids in which
   a. a cyclic olefin selected from the group consisting of cycloalkadienes and alkenylcycloalkenes is carbonylated to a cycloalkenyl carboxylic acid or ester by reaction with carbon monoxide and a hydroxylic compound selected from the group consisting of water, alcohols and phenols in the presence of a homogeneous catalyst composition consisting essentially of a mixture of a soluble palladium complex, a halide of aluminum and a substituted phosphine ligand which may constitute part of said palladium complex,
   b. the reaction mixture resulting from the above carbonylation reaction is heated to an elevated temperature under alkaline conditions without intermediate purification to induce cleavage of the cycloalkenyl ring, and
   c. the acyclic dicarboxylic acid is isolated from the reaction mixture.

3. A process as claimed in claim 2 in which the cyclic olefin is cyclo-octa-1,5-diene and the dicarboxylic acid is azelaic acid.

4. In a process for the preparation of carboxylic acids or esters in which an olefinically unsaturated compound is carbonylated by reaction with carbon monoxide and a hydroxylic compound selected from the group consisting of water, alcohols and phenols, the improvement wherein the carbonylation is carried out in the presence of a homogeneous catalyst composition consisting essentially of a mixture of a soluble palladium complex, a halide of aluminum and a substituted phosphine ligand, which optionally constitutes part of said palladium complex.

5. A process as claimed in claim 4 in which the atomic ratio of the aluminum to palladium is from 1:1 to 30:1.

6. A process as claimed in claim 4 in which the catalyst composition is a mixture of a chlorine-containing palladium compound and a chloride of aluminum.

7. A process as claimed in claim 4 in which the palladium compound is selected from the group consisting of bis(tri-arylphosphine)palladium dihalide, sodium tetrachloropalladite, $\pi$-allylpalladium halide dimer and tri-arylphosphinepalladium dihalide dimer.

8. A process as claimed in claim 7 in which the palladium compound is bis(triphenylphosphine)palladium dichloride.

9. A process as claimed in claim 4 in which the concentration of dissolved palladium is from $0.2 \times 10^{-3}$M to $3 \times 10^{-3}$M.

10. A process as claimed in claim 9 in which the unsaturated compound is selected from the group consisting of octene and styrene.

11. A process as claimed in claim 9 in which the unsaturated compound is a cyclic olefin.

12. A process as claimed in claim 11 in which the cyclic olefin is selected from the group consisting of cyclohexene, vinylcyclohexene, cyclo-octadiene, cyclododecene, cyclododecadiene and cyclododecatriene.

13. A process as claimed in claim 12 in which the cyclic olefin is cyclo-octa-1,5-diene.

* * * * *